(12) United States Patent
Kaiser et al.

(10) Patent No.: US 9,724,550 B2
(45) Date of Patent: *Aug. 8, 2017

(54) ONE PART, SOLIDS CONTAINING DECONTAMINATION BLEND COMPOSITION

(75) Inventors: Herbert J. Kaiser, Pontoon Beach, IL (US); Anchalee Thanavaro, Defiance, MO (US); Brandon W. Dell'Aringa, Bridgeton, MO (US); Bryan M. Tienes, Saint Louis, MO (US); Daniel A. Klein, Shiloh, IL (US); George W. Wagner, Elkton, MD (US)

(73) Assignees: American Sterilizer Company, Mentor, OH (US); The United States of America as represented by the Secretary of the Army, Washington, DC (US)

( * ) Notice: Subject to any disclaimer, the term of this patent is extended or adjusted under 35 U.S.C. 154(b) by 1242 days.

This patent is subject to a terminal disclaimer.

(21) Appl. No.: 11/504,172

(22) Filed: Aug. 15, 2006

(65) Prior Publication Data

US 2008/0045593 A1    Feb. 21, 2008

(51) Int. Cl.
| | | |
|---|---|---|
| *C11D 7/18* | (2006.01) | |
| *C11D 3/02* | (2006.01) | |
| *C07C 409/00* | (2006.01) | |
| *A62D 3/00* | (2006.01) | |
| *C11D 3/48* | (2006.01) | |
| *A62D 3/38* | (2007.01) | |
| *A61L 2/18* | (2006.01) | |
| *A61L 2/23* | (2006.01) | |
| *A62D 101/02* | (2007.01) | |

(52) U.S. Cl.
CPC ............... *A62D 3/38* (2013.01); *A61L 2/186* (2013.01); *A61L 2/23* (2013.01); *A61L 2202/24* (2013.01); *A62D 2101/02* (2013.01)

(58) Field of Classification Search
USPC ................................ 514/553, 557, 576, 714
See application file for complete search history.

(56) References Cited

U.S. PATENT DOCUMENTS

| 2,211,485 A * | 8/1940 | Frederick ...................... 424/490 |
|---|---|---|
| 3,969,257 A | 7/1976 | Murray |
| 4,016,090 A * | 4/1977 | Nakagawa et al. ...... 252/186.38 |
| 4,110,242 A * | 8/1978 | Hase et al. ............... 252/186.39 |
| 5,116,575 A * | 5/1992 | Badertscher et al. .......... 422/28 |
| 5,350,563 A | 9/1994 | Kralovic |
| 5,407,685 A | 4/1995 | Malchesky et al. |
| 5,662,866 A | 9/1997 | Siegel et al. |
| 6,369,288 B1 | 4/2002 | Brown |
| 6,468,472 B1 | 10/2002 | Yu et al. |
| 6,692,694 B1 | 2/2004 | Curry et al. |
| 2003/0060517 A1 | 3/2003 | Tucker et al. |
| 2003/0158459 A1 | 8/2003 | Tucker |
| 2004/0022867 A1 | 2/2004 | Tucker et al. |
| 2005/0153854 A1* | 7/2005 | Meyer et al. ................. 510/161 |
| 2005/0288203 A9 | 12/2005 | Brown et al. |

FOREIGN PATENT DOCUMENTS

| GB | EP 395333 | * 10/1990 |
|---|---|---|
| WO | WO 03/028429 | 4/2003 |

* cited by examiner

*Primary Examiner* — Shobha Kantamneni
(74) *Attorney, Agent, or Firm* — Hudak, Shunk & Farine Co. LPA

(57) ABSTRACT

A one part, solids containing decontamination blend composition comprises a solid acetyl donor coated with a compound that protects it from hydrolysis, a peroxygen source, optionally a catalyst, optionally a surfactant, and optionally a buffer. The decontamination blend composition is generally in a dry powder, particle, etc. form or in a tablet, pill, etc. form and is complete in and of itself in that no additional compounds are required prior to use and is readily distributed as a one package system. Upon the addition of water, a peroxygen compound such as hydrogen peroxide is formed, and peracetic acid is generated under alkaline conditions. The decontamination blend composition is particularly suitable for oxidizing various chemical and biological compounds thereby eradicating the same in situ as on surfaces, clothes, articles, and the like. Representative contaminants include mustard gas, nerve gas, bacterial toxins, anthrax, bird flu, and the like.

10 Claims, No Drawings

ONE PART, SOLIDS CONTAINING DECONTAMINATION BLEND COMPOSITION

FIELD OF THE INVENTION

The present invention relates to a one part, solids containing decontamination blend composition such that upon the addition of water thereto, peracetic acid and various peroxygen compounds are produced which readily decontaminate, via oxidation, surfaces, clothes, or articles contaminated with chemical and/or biological compounds that are often used in terrorism or warfare such as mustard gas, nerve gas, anthrax, various endospores, fungi, bacteria such as mycobacteria and vegetative bacteria, protozoa, and prions, viruses, and toxins such as ricin and T-2 mycotoxin. Additionally, the composition will readily decontaminate many of the known and emerging infectious diseases such as bird flu, C-difficile, etc., and also reduce the toxicity of toxic industrial materials and toxic industrial chemicals (TIMS and TICS respectively). The one part, ready to use packaged decontamination blend composition can exist as free flowing particles, powder, etc., or as tablets, pills, etc.

BACKGROUND OF THE INVENTION

Materials used in the decontamination of surfaces contaminated with chemical and biological warfare agents (CWA and BWA respectively), TICS, and TIMS are predominately liquid compositions, such as Decon Green™ developed by Edgewood Chemical Biological Center and Easy Decon™ developed by Sandia National Laboratories, the major active component of which is liquid hydrogen peroxide. The liquid, multi-component products have many inherent problems associated with them. The use, storage and transportation of high concentrations of hydrogen peroxide present many hazards and logistical challenges. High concentrations of hydrogen peroxide are highly corrosive, require special packaging, are limited in transportation modalities and are unstable without controlled storage and transportation systems.

The storage of large amounts of highly corrosive and heat sensitive liquids is a safety issue. Hydrogen peroxide spontaneously and irreversibly decomposes at elevated temperatures.

The use of multiple components requires accurately combining all components in the proper ratios each time the product is used. Short pot lives require complicated measuring every time the product is used or specially designed equipment to blend the product as it is being dispensed.

Many of these product types are incompatible with a number of substrates such as paints, soft metals, rubbers and plastics.

Many of these products contain a concentration of hydrogen peroxide subject to air shipment restrictions. In most cases, the products need to be shipped either by ground or sea causing delays in their arrival at required locations.

The thermodynamics of the combined components of many of these product types can cause "run-away" reactions to occur in certain circumstances and may require new dispensing equipment. Also, as the hydrogen peroxide degrades, foam can be produced which can spill from containers causing safety and chemical hazards.

SUMMARY OF THE INVENTION

The one part, solids containing decontamination blend composition of the present invention is a complete or unitary system in and of itself inasmuch as the solid such as a powder, particle, etc., only requires the addition of water thereto to generate decontamination compounds such as peracetic acid and peroxygen compounds that are very effective in destroying, killing, or eradicating chemical (warfare) and/or biological (warfare) agents such as anthrax, blister agents, nerve agents, various viruses, various endospores, fungi, bacteria such as mycobacteria and vegetative bacteria, protozoa, prions, bacterial toxins such as ricin, T-2 Mycotoxins and other infectious diseases such as bird flu, C-difficile, MRSA, etc., as well as toxic industrial chemicals and toxic industrial materials.

An important aspect of the present invention is the use of an acetyl donor that is coated with a hydrolysis resistant or preferably an alkaline hydrolysis resistant coating such as various organic acids, weak mineral acids such as boric acid, various cellulose compounds, conventional pharmaceutical coatings, and the like. Desirably the coating also provides acidity to help adjust and buffer the pH of the end-use diluted decontamination blend composition. A solid inorganic peroxygen source such as a peroxo-compound or an organic/inorganic compound that can generate a peroxo-compound in situ is also utilized. A preferred peroxygen source is sodium percarbonate. A catalyst is optionally utilized to ensure stability as well as to catalyze oxidation reactions of the peracetic acid and the peroxygen with the chemical or biological agent in order to destroy, kill, or eradicate the same. Catalysts include salts of various transition metals. Optionally a surfactant such as an anionic, nonionic, cationic, or amphoteric surfactant can be utilized. An optional buffer can also be utilized to maintain the alkalinity of the system such as from a pH of 7 to about 13. Desirably the buffer will also react with the acid coating and generate carbon dioxide that will assist in the dissolution and mixing of the solids containing decontamination composition.

DETAILED DESCRIPTION OF PREFERRED EMBODIMENTS OF THE PRESENT INVENTION

The one part, solids containing decontamination blend composition of the present invention is a blend of different solid compounds that exist as a one part system or as a single package that is complete in and of itself. Thus, the present invention provides ease of transportation of the decontamination composition since water is not transported. The decontamination composition is also relatively safe since active components and/or corrosive components are not contained therein such as peracetic acid and a peroxygen compound, is readily stored, and has good shelf stability as packaged or when mixed with water. Desirably, at the point of application the decontamination composition is mixed with water, whereupon oxidizing agents such as peracetic acid and peroxygen compounds are generated, and are applied to various chemical and/or biological contaminated surfaces, clothes, or articles.

The acetyl donor is a source of peracetic acid (PAA) that is formed upon the addition of water to the one part, solids containing decontamination blend composition. Upon the addition of water, peracetic acid is formed by reaction of the acetyl donor with the peroxygen source in the presence of an alkaline medium often provided by the buffer. Generally, any compound that functions as an acetyl group donor is suitable. Such acetyl donors include acetylsalicylic acid (aspirin), acetic anhydride, tetraacetylethylenediamine (TAED), pentaacetyl glucose, acetylcholine, acetyl borate derivatives, and the like, as well as combinations thereof. Acetylsalicylic acid and tetraacetylethylenediamine are preferred.

The total amount of the one or more acetyl donors is generally from about 10% to about 70% by weight, desirably from about 15% to about 55% by weight and preferably from about 20% to about 35% by weight based upon the total weight of all of the compounds that form the one part, solids containing decontamination blend composition. By definition the one part, solids containing decontamination blend composition includes the one or more acetyl donors, the one or more coating compounds, the one or more peroxygen sources, the one or more optional catalysts when utilized, the one or more optional surfactants when utilized, and the one or more optional buffers when utilized. While other components can also be utilized in the composition such as various additives, fillers, colorants, and the like, they are not included as the bases upon which the amounts of the various compounds of the one part, solids decontamination blend composition are calculated.

An important aspect of the present invention is the utilization of at least one coating compound applied to the acetyl donor, the primary function of which is to protect the solid acetyl donors from hydrolysis including alkaline hydrolysis. That is, the coating prevents the peroxygen source as well as the buffer from reacting with the acetyl donor thus forming a complete or unitary decontamination composition wherein all compounds are contained within the blended decontamination composition package. The coating can also be utilized to provide acidity to help adjust and buffer the pH of the composition when diluted with water. Yet another coating function is that upon the application of water, the coating reacts with buffer compounds such as carbonates and bicarbonates to produce carbon dioxide and provide effervescence that aids in the dispersion, dissolution and mixing of the various composition compounds.

The coating can be selected from a large group of compounds including organic acids such as carboxylic acids having 1 to 3 or 4 acid groups and from 1 to 20 carbon atoms and a pKa of 4.0 or greater that include citric acid, salicylic acid, tartaric acid, $C_2$ through $C_8$ dicarboxylic acids such as oxalic acid, malonic acid, succinic acid, glutaric acid, adipic acid, maleic acid, and the like. Weak mineral acids can also be utilized such as boric acid. Other compounds include conventional pharmaceutical compounds that are utilized in coating various tablets, pills, and the like such as cellulosic compounds as for example hydroxy propyl methyl cellulose, hydroxypropyl cellulose, hydroxyethyl cellulose, ethyl cellulose, acetyl cellulose, benzyl cellulose, cellulose acetobutylate, cellulose acetylphthalate, and the like. Still other pharmaceutical coating compounds include long chain soluble alcohols such as polyvinyl alcohol, mixtures of fatty acids and/or fatty acid salts, as well as various resins and polymers such as polymethyl methacrylate copolymer, various acrylic resins, lactic acid and/or glycolic acid oligomers, polyethylene glycols, polyvinyl pyrolidones, polycaprolactones, various polyorthoesters, various polyanhydrides, and the like. Still other suitable pharmaceutical coating compounds include various gelatins, various maltodextrins, various sugars, and various latexes. All of these coatings materials are known to the art and to the literature. Citric, boric, and salicylic acids are preferred coating materials.

The amount of the one or more coating materials utilized is from about 1% to about 20% by weight, desirably from about 1.25% to about 15% by weight and preferably from about 1.5% to about 5% or about 10% by weight based upon the total weight of the above-specified compounds which form said one part, solids containing decontamination blend composition.

Another ingredient of the one part, solids containing decontamination blend composition is a peroxygen source. Such compounds are various inorganic peroxo-compounds or various organic/inorganic compounds that can generate peroxo-compounds in situ. Examples of suitable peroxygen sources include sodium or potassium percarbonate or other percarbonate salts, sodium or potassium perborate or other perborate salts, calcium peroxide, magnesium peroxide, sodium or potassium persulfate or other persulfate salts, urea peroxide, potassium monopersulfate (oxone), peroxydone, and the like. Generally peroxygen sources include percarbonates and perborates, and desirably combinations of percarbonates and perborates. Sodium percarbonate is a preferred peroxygen source inasmuch as it produces hydrogen peroxide, a preferred peroxygen compound.

The amount of the one or more peroxygen sources generally varies from about 10% to about 70% by weight, desirably from about 15% to about 60% by weight, and preferably from about 20% or about 30% to about 45% or about 50% by weight, based upon the total amount of the above-specified compounds which form the one part, solids containing decontamination blend composition.

Metal catalysts are optionally, but desirably utilized to aid the peracetic acid and the peroxygen compound in the presence of alkalinity to oxidize and eradicate or destroy chemical or biological compounds often utilized as warfare agents. Such catalysts include non-transition metal catalysts, non-metal catalysts, and transition metal catalysts. Examples of transition metal catalysts include salts of molybdenum, vanadium, titanium, iron, copper, and other transition metals that have historically been used for oxidation reactions and the same are well known to the literature and to the art. Preferred catalysts are the various molybdate compound such as sodium molybdate, potassium molybdate, and ammonium molybdate.

The amount of the one or more optional catalysts is generally from about 0.1% to about 6.0% by weight, desirably from about 0.3% to about 4.0% by weight, and preferably from about 0.5% to about 3.0% by weight based upon the total weight of the above-specified compounds that form the one part, solids containing decontamination blend composition.

For efficacy in decontamination, surfactants or wetting agents are optionally utilized for optimal contact with the chemical or biological agents, that can often be utilized in warfare, and for removal of the chemical or biological agents and their degradants from surfaces. The surfactants should also be low foaming. In general, nonionic surfactants are better wetting and emulsifying agents than other types such as anionics, cationics, and amphoterics, and thus are preferred. The surfactants contribute to the wetting of surfaces and soils by lowering the surface tension. This wetting of the surface/soil allows the active compounds such as peracetic acid and the peroxygen a more facile route to reaction with the chemical agent and biological agent substrates and also allows penetration into cracks and crevices. The surfactants also function as detergents since they lift chemical and biological agents from a surface and allow the oxidizing agent to eradicate the same and to remove the agent upon rinsing. The suitable dispersal of the powdered decontaminant in water is an additional advantage of using surfactants in the decontamination composition.

Anionic, nonionic, amphoteric/zwitterionic, and cationic surfactants can be used in the system alone or in appropriate combinations and the same are numerous and are known to the literature and to the art. Examples of nonionic surfactants include but are not limited to various alcohol ethoxylates or alcohol propoxylates, or combinations thereof, such as R—O-(EO)$_m$(PO)$_n$—R' where m is 0 or 1 to 10 and n is 0 or from 1 to about 10, R is a primary or secondary alcohol having a total of from 1 to about 20 carbon atoms and R' is an alkyl having from 1 to about 5 carbon atoms and preferably is hydrogen. Other examples include fatty alcohol polyglycol ethers, nonylphenoxypoly (ethyleneoxy) ethanol, and ethoxylated polyoxypropylene. Specific examples of non-ionics include Igepal CO-730 (nonylphenoxypoly(ethyleneoxy)ethanol), Pluronic 25R4 (block copolymers of ethylene oxide and propylene oxide), Pluronic L10 (block copolymers of propylene oxide and ethylene oxide), Tergitol 15-S-20 ($C_{12}$-$C_{14}$ secondary alcohol ethoxylate), Tergitol 15-S-30 ($C_{12}$-$C_{14}$ secondary alcohol ethoxylate), Tergitol XH (ethylene oxide propylene oxide copolymer) and Tomadol 25-12 ($C_{12}$-$C_{15}$ linear primary alcohol ethoxylate). Examples of anionic surfactants include but are not limited to sodium lauroyl sulfate, sodium polyacrylate, sodium lauroyl sarcosinate, and sodium xylene sulfonate. Examples of cationic surfactants include but are not limited to benzalkonium chloride, benzethomium-chloride, dodecyltrimethylammonium chloride, and hexadecyl pyridinium chloride. The surfactants set forth above or others can be used alone or in combination with each other.

The amount of one or more optional surfactants is generally from about 0.01% to about 10.0% by weight, desirably from about 0.5% to about 6.0% by weight, and preferably from about 1.0% to about 4.0% by weight based upon the total weight of the above-specified compounds that form the one part, solids containing decontamination blend composition.

The one part, solids containing decontamination blend composition comprises one or more optional but desirable buffers. Buffers are utilized to buffer the system and thus maintain an alkaline pH of the solution when mixed with water. A desirable pH is from 7 to about 13 with a pH of from 7 to about 10 being preferred. When the coating compound is an acid, the buffer will also react therewith to generate carbon dioxide. As noted above, carbon dioxide produces fizzing or effervescence and thus serves to promote physical mixing of the various compounds to increase reaction between the same. Various salts of carbonate and bicarbonate are preferred such as the potassium or sodium salts thereof. Another preferred buffer is the various borates such as borax and puffed borax. Other buffers include weak organic acids having from 1 to about 20 carbon atoms, and various phosphates. Weak organic acids generally have a low PKa of from about 4 to about 10 or about 15 with examples including citric acid, salicylic acid, and the like. Thus, carboxylic acids serve both as a buffer compound and as a coating for the acetyl donor. The utilization of a buffer is usually important in order to maintain an alkaline pH of the decontamination composite blend once diluted with water.

The amount of the one or more optional buffers is generally from about 5% to about 50% by weight, desirably from about 10% to about 40% by weight, and preferably from about 15% to about 35% by weight based upon the total weight of the above-specified compounds that form the one part, solids containing decontamination blend composition.

Co-solvents are optionally utilized in order to improve the solubility of the chemical agent or the biological agent in the water diluted composition so that such agents can be more easily oxidized. Solvents can also be utilized to extract the chemical or biological agents from paints and coatings such as Chemical Agent Resistant Coatings (CARC). Solid solvents that can be initially added to the one part, solids containing decontamination blend composition include sulfones or carbonates such as dimethyl sulfone and ethylene carbonate. Liquid solvents include various glycols having a total of from 2 to about 8 carbon atoms such as propylene glycol and hexylene glycol or propylene carbonate.

The use of liquid solvents in the one part, solids containing decontamination blend composition however poses a challenge in keeping the one part system generally dry. A solution is the use of puffed borax to absorb the liquid solvents. For example, about 20 grams to about 30 grams of solvent can be sprayed onto 100 grams of puffed borax while stirring to give a free flowing powder of approximately 15% to about 28% solvent. The puffed borax can be stirred in a mixer and the solvent such as propylene carbonate added utilizing a standard pump sprayer. More viscous solvents such as propylene glycol and hexylene glycol can be used at lower loading concentrations to maintain a free flowing powder.

An important aspect of the present invention is that the decontamination composition is a one part solids containing blend. That is, the composition is generally a blend of free flowing powders and/or particles, often contained in a package, or in the form of an integral, solid article such as a plurality of pills, pellets, large granules, pebbles, nuggets, small blocks, and the like. Accordingly, so long as the composition can freely flow or maintain its pellet, pill, nugget, etc, size, small amounts of a solvent such as water can generally be added up to an amount of about 20% by weight based upon the total weight of the decontamination composition including fillers, additives, etc. Desirably the amount of water utilized is about 15% or less by weight, more desirably 10% or less by weight, preferably about 5% by weight or less, and more preferably nil. In summary, solvents such as water are not desired because of the added weight they impart to shipping of the decontamination process and more importantly since they can prematurely cause various compounds to react and prematurely form peracetic acid or peroxygen compounds such as hydrogen peroxide.

The one part, solids containing decontamination blend composition of the present invention can be readily made by adding the above-noted compounds in the above-noted amounts together in any order and mixing the same. With regard to the acetyl donor, it is important that the same be coated with one or more of the above-noted coating materials before being blended with the remaining compounds. A specific example of coating the acetyl donor is set forth below utilizing only one coating material and one acetyl donor to demonstrate the present invention. However, the coating process is by no means limited to the following example inasmuch as many other different types of coating processes are available such as spray drying, top spray fluid bed, etc.

Acetylsalicylic acid (aspirin) was coated with citric acid in the following manner using a Wurster-type coating apparatus. Aspirin of particle sizes between 20 and 50 U.S. standard mesh are isolated using sieves. A concentrated solution of citric acid is prepared (approximately 50% by weight in water). The solution can also contain surfactants as wetting agents to improve the coating uniformity or polymers to improve coating integrity. The apparatus is warmed up to an inlet temperature of approximately 77° C. The fluidizing air is set to a value that will produce a fluidized powder pattern consistent with the Wurster process. The coating apparatus is charged with the sieved aspirin until it covers approximately ½ of the inner partition tube. The weight of aspirin necessary for this fill level is recorded. The fluidizing air and heater are switched back on and the nebulizer air pressure is set to give a good spray pattern. Intermittent bursts of air are used to keep the filter bags clear. The coating solution is added using a peristaltic pump at a rate just slow enough to keep the powder properly fluidized. The weight of solution added to the process is monitored and stopped when the appropriate amount has been added. The outlet temperature is maintained at 49° C. to 52° C. by adjusting the inlet air temperature. After all of the coating solution is added the powder is allowed to dry until the outlet temperature starts to increase. The coated aspirin particles are then removed.

Upon discovery of a chemical or biological toxicant or agent, or warfare agent, the one part, solids containing decontamination blend composition of the present invention as in the form of a package containing either free flowing powder, etc., or solid pills, etc., is delivered to the discovered toxic site. Preferably, at that site, the composition is diluted with water to a desired amount. Naturally, concentrated solutions or diluted solutions can be made. Thus, the amount of water added can generally range from about 100 to about 4,000 parts by weight, desirably from about 200 to about 2,000 parts by weight and preferably from about 500 to about 1,000 parts by weight per every 100 parts by weight of the decontamination composition blend including any additives or fillers. It is to be understood that many other ranges can be utilized and that those set forth herein relate to the expected concentration usage. Upon the addition of water to the one part, solids containing decontamination blend composition, the acetyl donor coating such as citric acid or borax is dissolved. The water will react with the peroxygen source and generate hydrogen peroxide. The generated hydrogen peroxide will react with the acetyl donor in the presence of the alkaline compound such as the buffer to form peracetic acid. The remaining unreacted percarbonate will act as a buffer. The water additionally reacts with the buffer to produce fizzing or effervescence that promotes mixing of the various components to mix with one another and react. The net result is an aqueous solution containing high amounts of peracetic acid therein as well as hydrogen peroxide. Depending upon the amount of acetyl donors utilized and the amount of the peroxygen source, the concentration of the peracetic acid can generally range from about 0.5% to about 10% or 15% by weight, desirably from about 0.5% to about 5% by weight, and preferably from about 1% to about 3% by weight based upon the total weight of the decontamination composition, including additives, fillers and water. The amount of the peroxygen compound generated such as hydrogen peroxide can also range widely such as from about 0.5% to about 10% or about 15% by weight, desirably from about 0.5% to about 5% by weight, and preferably from about 1% to about 3% by weight of the decontamination composition including additives, fillers, and water. The aqueous decontamination composition solution is then applied to the chemical or biological agent whereby the agent is oxidized and destroyed, eradicated, or rendered harmless, and the like.

Various non-limiting specific compounds that can be utilized with regard to each type of compound (e.g. acetyl donor, peroxygen source, etc.) are set forth in Table 1.

TABLE 1

Compounds, ingredients and concentration ranges

| | | | Weight % based upon the total weight of the one part, solids decontamination blend composition excluding additives, fillers, etc. | |
|---|---|---|---|---|
| Ingredient | CAS | Use | Low % | High % |
| PEROXYGEN SOURCE | | | 10 | 70 |
| Sodium Percarbonate | 15630-89-4 | $H_2O_2$ source | 10 | 70 |
| Sodium Perborate | 7632-04-4 | $H_2O_2$ source | 10 | 70 |
| Urea Peroxide | 124-43-6 | $H_2O_2$ source | 10 | 70 |
| Oxone (Potassium Monopersulfate) | 37222-66-5 | $H_2O_2$ source | 10 | 70 |
| Peroxydone ($H_2O_2$ polymer) | | $H_2O_2$ source | 10 | 70 |
| BUFFER | | | 5 | 50 |
| Potassium bicarbonate | 298-14-6 | Buffer | 5 | 50 |
| Potassium carbonate | 584-08-7 | Buffer | 5 | 50 |
| Borax | 1303-96-4 | Buffer/PAA stabilizer | 5 | 50 |
| Puffed Borax | | Buffer/PAA stabilizer/ solvent carrier | 5 | 50 |
| COSOLVENT | | | | |
| Propylene glycol | 57-55-6 | Solvent absorbed in puffed borax | | |
| Propylene carbonate | 108-32-7 | Solvent absorbed in puffed borax | | |
| Hexylene glycol | 107-41-5 | Solvent absorbed in puffed borax | | |
| CATALYST | | | 0.1 | 6 |
| Sodium Molybdate | 7631-95-0 | catalyst | 0.1 | 6 |
| Potassium Molybdate | 13446-49-6 | catalyst | 0.1 | 6 |
| Ammonium Molybdate | 13106-76-8 | catalyst | 0.1 | 6 |
| ACETYL DONOR | | | 10 | 70 |
| Aspirin | 50-78-2 | Peroxide Activator/ PAA generator | 10 | 70 |
| TAED | 10543-57-4 | Peroxide Activator/ PAA generator | 10 | 70 |

TABLE 1-continued

Compounds, ingredients and concentration ranges

| Ingredient | CAS | Use | Weight % based upon the total weight of the one part, solids decontamination blend composition excluding additives, fillers, etc. | |
|---|---|---|---|---|
| | | | Low % | High % |
| Acetylcholine Cl | 60-31-1 | Peroxide Activator/ PAA generator | 10 | 70 |
| Pentaacetyl glucose | 604-68-2 604-69-3 | Peroxide Activator/ PAA generator | 10 | 70 |
| COATING | | | 1 | 20 |
| Citric Acid | 77-92-9 | pH adjuster/aspirin coating | 1 | 20 |
| Boric Acid | 11113-50-1 | pH adjuster | 1 | 20 |
| SURFACTANT | | | 0.01 | 10 |
| Nonionic surfactant | | | 0.01 | 10 |
| Igepol CO-730 (Nonylphenoxy-poly(ethyleneoxy)ethanol) | 9016-45-9 | Agent solubilizer/ wetting | 0.01 | 10 |
| Pluronic 25R4 (Block copolymers of ethylene oxide and propylene oxide) | 9003-11-6 | Agent solubilizer/ wetting | 0.01 | 10 |
| Pluronic L10 (Block copolymers of propylene oxide and ethylene oxide) | 9003-11-6 | Agent solubilizer/ wetting | 0.01 | 10 |
| Tergitol 15-S-20 ($C_{12}$-$C_{14}$ secondary alcohol ethoxylate) | 84133-50-6 | Agent solubilizer/ wetting | 0.01 | 10 |
| Tergitol 15-S-30 ($C_{12}$-$C_{14}$ secondary alcohol ethoxylate) | 84133-50-6 | Agent solubilizer/ wetting | 0.01 | 10 |
| Tergitol XH (Ethylene oxide propylene oxide copolymer) | 106392-12-5 | Agent solubilizer/ wetting | 0.01 | 10 |
| Tomadol 25-12 ($C_{12}$-$C_{15}$ linear primary alcohol ethoxylate) | 68131-39-5 | Agent solubilizer/ wetting | 0.01 | 10 |
| TAM-25 (Ethoxylated fatty amines) | 61791-26-2 | Agent solubilizer/ wetting | 0.01 | 10 |
| | | | 0.01 | 10 |
| Anionic surfactant | | Agent solubilizer/ wetting | 0.01 | 10 |
| Sodium lauroyl sulfate | 17404-70-5 | Agent solubilizer/ wetting | 0.01 | 10 |
| Sodium polyacrylate | | Agent solubilizer/ wetting | 0.01 | 10 |
| Sodium lauroyl sarcosinate | 137-16-6 | Agent solubilizer/ wetting | 0.01 | 10 |
| Sodium xylene sulfonate (solid) | 1300-72-7 | Agent solubilizer/ wetting | 0.01 | 10 |
| | | | 0.01 | 10 |
| Cationic surfactant | | Agent solubilizer/ wetting | 0.01 | 10 |
| Benzalkonium chloride | 8001-54-5 6839-01-05 68424-85-1 85409-22-9 61789-71-7 | Agent solubilizer/ wetting | 0.01 | 10 |
| Benzethonium chloride | 121-54-0 | Agent solubilizer/ wetting | 0.01 | 10 |
| Dodecyltrimethylammonium chloride | 112-00-5 | Agent solubilizer/ wetting | 0.01 | 10 |
| Hexadecyl pyridinium chloride | 123-03-5 | Agent solubilizer/ wetting | 0.01 | 10 |

The present invention can be utilized to decontaminate or more specifically oxidize various chemical and biological compounds in order to render them harmless, ineffective, and the like. Examples of chemical compounds include mustard gas, e.g. HD, i.e. bis(2-chloroethyl) sulfide; nerve gas, e.g. VX, that is S-[2-[bis-(1-methylethyl)amino]ethyl] o-ethyl-methyl phosphonothioic acid ester, soman, that is 1,2,2-trimethylpropyl methylphosphonofluoridic acid ester, blister agents, and the like. Other chemical compounds include toxic industrial chemicals/toxic industrial materials (TICS/TIMS) such as phosphorous pesticides, as well as organo phosphorous pesticides, and the like. Biological compounds include anthrax, various viruses including bird flu viruses, polio virus, small pox virus, pneumonia, HIV, C-difficile, and the like; endospores, fungi, bacteria such as mycobacteria and vegetative bacteria, protozoa, prions, and toxins such as ricin and T-2-nycotoxin.

Examples of biological compounds include spores such as endospores, fungi, bacteria such as mycobacteria and vegetative bacteria, protozoa, and prions. Examples of endospores include *Geobacillus stearothermophilus, Bacillus subtilis, Bacillus subtilis globigil, Clostridium sporogenes, Bacillus cereus*, and *Bacillus circulans*. Examples of fungi include *Aspergillus niger, Candida albicans*,

*Trichophyton mentagrophytes*, and *Wangiella dermatitis*. Examples of mycobacteria which can be utilized in the present invention include *Mycobacterium chelonae*, *Mycobacterium gordonae*, *Mycobacterium smegmatis*, and *Mycobacterium terrae*. Examples of vegetative bacteria include *Aeromonas hydrophila*, *Enterococcus faecalis*, *Streptococcus faecalis*, *Enterococcus faecium*, *Streptococcus pyrogenes*, *Escherichia coli*, *Klebsiella* (pneumoniae), *Legionella pneumophila*, *Methylobacterium*, *Pseudomonas aeruginosa*, *Salmonella choleraesuis*, *Helicobacter pylori*, *Staphylococcus aureus*, *Staphylococcus epidermidis*, and *Stenotrophomonas maltophilia*. Examples of protozoa include *Giardia lamblia* and *Cryptosporidium parvum*. Examples of prions include infectious proteins.

With regard to actually testing mustard gas, since the same is highly toxic, thioanisole is an acceptable substitute thereof. Since thioanisole is less soluble than mustard gas, it serves as a good test analogy.

The effectiveness of the decontamination compositions of the present invention with regard to chemical agents and chemical warfare agent can be determined by either a reactive test procedure or a panel test procedure. The reactor test is a solution test whereas the panel test evaluates the effectiveness of the proposed decontamination compositions when the chemical or biological agent is present on a surface as most likely it would be in the case of a chemical or biological attack.

For each test the simulant was a 5% (w/w) solution of n-dodecane prepared in thioanisole. The n-dodecane functioned as an internal standard. All decontamination compositions were added to deionized water. However, the decontamination compositions can be prepared in any quality of water including but not limited to deionized, distilled, softened, hard, tap, river, and sea waters. The resulting mixture was stirred for 20 minutes prior to use at room temperature.

The reactor test comprises placing the simulant (100 µL, 0.85 mmol) in a 4-dram vial. The decontaminant composition solution (5 mL) was added to the 4-dram vial containing the simulant. The resulting mixture was agitated on a shaker at a temperature of about 20° C. At the desired time, the reaction mixture was quenched with 5 mL of saturated sodium sulfite ($Na_2SO_3$) and extracted with 5 mL chloroform (0.1% tetrahydrothiophene) using a vortex mixer (2×15 sec.). The chloroform layer was then transferred to a sample vial and analyzed by GC-MS (gas chromatograph-mass spectrophotometer).

The panel test comprises using two-inch diameter CARC painted aluminum discs used as received from Edgewood Chemical Biological Center. The panel was contaminated at 10 g/m² by adding approximately 20 mg of thioanisole using an Eppendorf pipette. Droplets were spread with thin strip of parafilm. The panel was then covered with an inverted Petri dish and allowed to stand at room temperature for 60 minutes. The decontamination composition solution (1 mL) was pipetted over the surface of the panel and allowed to stand for 15 minutes, covered. The excess decontaminant was decanted and the panel was rinsed with 40 mL of deionized water on the front and 20 mL of deionized water on the back. The panel was set in a vertical position to dry. The panel was then extracted with 20 mL of chloroform (containing 0.1% tetrahydrothiophene) for 1 hour. The undiluted chloroform was analyzed by GC-MS.

With regard to biological agents, since testing for anthrax is extremely dangerous and cannot be handled in any laboratory less than a Class 3, *Bacillus subtilis*, ATCC 19659 can be used as a surrogate for anthrax. Two screening procedures can be used for the effectiveness of various decontamination compositions: a Time Kill Suspension Test and a modified AOAC Sporicidal Activity Test (known here, as the Quantitative Sporicidal Activity Test (QSAT)).

The Time Kill Suspension Test comprises using pre-prepared spore cultures used from Presque Isle Cultures of *Bacillus subtilis*, ATCC 19659, and *Bacillus stearothermophilus*, ATCC 7953. Test cups were prepared with 9.9 mL of the decontamination composition of the present invention to be tested. Control solutions were prepared containing only Butterfield's buffer for evaluation on the test day. To each test article, 0.1 mL of prepared chemical or biological agent was added while starting the timer simultaneously. The samples were mixed thoroughly. At the appropriate contact times, 0.1 mL of the appropriate test article was placed into 9.9 mL of the appropriate biological decontaminant and mixed thoroughly. Ten-fold serial dilutions were performed through $10^{-6}$ and plated using the aerobic plate count method. Plates were incubated at approximately 37° C. Plates were incubated 2 days at 37±2° C. by *B. subtilis* and at 55±2° C. for *B. stearothermophilus*. Following incubation, colony forming units (CFU) were counted using standard plate count techniques and converted to $log_{10}$ values for analysis.

The QSAT (Quantitative Sporicidal Activity Test) comprises using porcelain, silk, and polyester carriers or substrates purchased from Presque Isle Cultures prepared with *B. subtilis*, ATCC 19659. An appropriate amount of the decontamination composition was prepared. Each analysis required preparation of enough of the decontamination composition for the test immediately before testing, then dispensing in the appropriate aliquots. The carriers were then placed into 10 mL of test product and a timer was started. At appropriate contact times the carrier was removed and placed into the biological composition. When performing a quantitative test, tubes were sonicated for 5 minutes and vortexed for 30 seconds. Following sonication 10 fold serial dilutions to $10^{-6}$ were performed and plated using aerobic plate count method. Plates were incubated for 2-3 days at 37±2° C. before counting CFUs using standard plate count methods. Carriers were submerged in fresh broth and incubated for 6 days before scoring for positive or negative growth. CFU counts converted to $log_{10}$ values for analysis.

With respect to actual LIVE AGENTS, panel testing is utilized according to the following general procedure of Chemical Agent Application, Decontamination, and Residual Agent Measurement.

Chemical Agent Application

Test coupons were allowed to equilibrate to the ambient laboratory temperature (20° C.) for a minimum of 10 minutes prior to agent application. Test coupons were placed horizontally in the chemical agent fume hood. Chemical agents were applied to the test coupons to achieve a contamination density of 10 g/m². The coupons were covered with a glass petri dish cover Decontamination One hour after chemical agent application, the test coupons were decontaminated in a horizontal orientation by pipetting on 1 mL of the liquid decontamination composition. Coupons were covered with a petri dish. Contact time of decontaminant on the contaminated test coupon was 15 minutes. Six replicates were performed for each treatment. Coupons were rinsed with water at ambient room temperature to remove the decontamination composition prior to measurement of residual agent. Water (40 mL) was dispensed from a dispenser approximately 2 inches from the coupon surface, followed by a 20 mL water rinse of the coupon back. The coupon was rinsed from top to bottom, and all surfaces of the test coupon were rinsed. The coupons were placed in a near-vertical orientation on a clean surface and allowed to air dry for 3 minutes prior to initiation of contact hazard assessment.

Residual Agent Measurements can be Determined by either Contact Transfer or Coupon Extraction Contact Transfer Contact transfer was determined at two fifteen-minute intervals, from 0-15 minutes and 45-60 minutes following decontamination. The coupon was placed on a clean horizontal surface controlled at 300±2° C. A 2-inch diameter piece of latex was placed on the test coupon as a sampler. A 2-inch diameter piece of aluminum foil was placed on the latex, and a 2-inch diameter insulated weight (1 kg) was placed on the aluminum foil. After 15 minutes of contact, the weight was removed. The latex and aluminum foil were placed in a vial containing 20 mL of chloroform for one hour. Tetrahydrothiophene was added at 0.1 volume percent to all chloroform used for extraction to quench any residual oxidant. After the first contact transfer measurement, the coupons were kept at 30° C. and covered with a petri dish cover. A second contact transfer measurement was conducted at 45-60 minutes following decontamination using the same procedure. After a 60-minute extraction period for the latex and aluminum foil, an undiluted aliquot of chloroform was transferred to a GC vial for analysis. The sample was analyzed for chemical agent using a gas chromatograph equipped with a flame ionization detector.

Coupon Extract

The coupon used for the contact tests was immediately placed in a glass extraction dish and extracted in 20 mL. of chloroform. After a 60-minute extraction, an undiluted aliquot of chloroform was transferred to a GC vial for analysis. The sample was analyzed for chemical agent using a gas chromatograph equipped with a flame ionization detector.

EXAMPLES

The following Examples relate to various one part, solids containing decontamination blend compositions of the present invention in water and serve to illustrate but not to limit the present invention.

Formula 1 was prepared using boric acid and citric acid to coat aspirin in a manner set forth herein above and then the compounds in the noted amounts were dry blended and subsequently added to 100 mL of water. The one part, solids decontamination composition of formula 3 was then tested with regard to soman and results monitored by $^{31}$P-NMR (Phosphorous 31-Nuclear Magnetic Resonance).

| Formula 1 | |
|---|---|
| Ingredient | g/100 mL |
| Sodium percarbonate | 3.850 |
| Potassium bicarbonate | 1.925 |
| Tergitol XH | 0.300 |
| Sodium molybdate | 0.060 |
| Boric acid | 0.225 |
| Citric acid | 0.225 |
| Aspirin | 2.700 |

TABLE 1

Reactor test results using thioanisole as the simulant. (Formula 1)

| Time (min) | Run 1 (% Decontamination) | Run 2 (% Decontamination) | Run 3 (% Decontamination) | Average |
|---|---|---|---|---|
| 5 | 80.26 | 74.97 | 76.57 | 77.27 |
| 15 | 91.82 | 89.99 | 89.35 | 90.39 |
| 30 | 99.81 | 99.78 | 99.70 | 99.76 |

As apparent from Table 1, the utilization of decontamination composition Formula 1 resulted in at least 99% by weight eradication of thioanisole which is a simulate with respect to mustard gas.

Additionally, Formula 6 which is found hereinafter in Table 4 is prepared in a similar manner and the results thereof with respect to soman are set forth in Table 2.

TABLE 2

Results of testing against soman (GD)

| Time (min) | Formula 1 | Formula 6 | Decon Green ™ |
|---|---|---|---|
| 1 | 76% | 99.9% | 60% |
| 2 | 81% | 99.9% | 86% |
| 3 | 89% | 100% | 99.9 |
| 4 | 89% | — | 100% |
| 5 | 91.8* | — | — |
| 8 | 97.3% | — | — |
| 15 | 98.1% | — | — |

As apparent from Table 2, Formula 1 showed a high amount of oxidation that is eradication of at least 98% by weight of the chemical agent in only 15 minutes whereas Formula 6 achieved an extraordinary eradication of at least 99% within 1 minute!

The decontamination composition of Formula 1 was also tested with respect to *Bacillus subtilis* spores and Decon Green™ for comparative purposes. Decon Green™ is a commercially available decontaminate which generally has the following formulation: 10 vol % propylene carbonate (99%), 20 vol % propylene glycol (99.5+%), 10 vol % Triton X-100, 30 vol % 35% $H_2O_2$, 30 vol % distilled water solution containing salts (4 vol % propylene glycol added as antifreeze), 0.45 M potassium bicarbonate (potassium hydrogen carbonate, 99.7%), 0.25 M potassium citrate monohydrate (99+%), and 0.01 M potassium molybdate (98%). Log reduction times are set forth in Table 3.

TABLE 3

Results of testing against Bacillus Subtilis

| Sample | Time (min) | Log Reduction | Sample | Time (min) | Log Reduction |
|---|---|---|---|---|---|
| Formula 1 | 0.5 | .025 | Decon Green ™ | 5 | 1.51 |
|  | 1 | 1.83 |  | 10 | 2.42 |
|  | 2 | 4.82 |  | 15 | 4.91 |

As readily apparent from Table 3, the decontamination composition of the present invention achieved a log reduction with at least 4.82 in only 2 minutes, whereas the Control, in Decon Green™ achieved a similar log reduction in 15 minutes. Thus, the data once again sets forth the fact that the present invention rapidly destroys chemical and biological agents and thus easily surpasses the performance of current technology.

Additional examples of different decontamination composition formulas in accordance with the present invention are set forth in Table 4 wherein Formulations 2-6 were tested for 15 minutes, with regard to the decomposition of thioanisole.

TABLE 4

Example formulas. Results of testing against Thioanisole

|  | Formula 2 | Formula 3 | Formula 4 | Formula 5 | Formula 6 |
|---|---|---|---|---|---|
|  |  |  | g/100 mL |  |  |
| Sodium Percarbonate | 4.650 | 4.650 | 4.650 | 3.850 | 3.850 |
| Potassium Bicarbonate | 5.000 | — | 5.000 | 1.925 | 1.925 |
| Puffed Borax (81%) Propylene Glycol (19%) | — | 3.000 | — | — | — |
| Tergitol XH | 0.300 | — | 0.300 | 0.300 | 0.100 |
| Sodium Lauroyl Sarcosinate | 0.015 | 0.015 | 0.015 | — | — |
| Dodecyltrimethyl ammonium Chloride | — | — | — | — | 0.500 |
| Sodium Molybdate | 0.240 | 0.240 | 0.240 | 0.060 | — |
| Boric Acid | 0.170 | 0.170 | — | 0.225 | 0.225 |
| Citric Acid | 0.170 | 0.170 | 0.251 | 0.225 | 0.225 |
| Aspirin | 3.450 | 3.450 | 3.450 | 2.700 | 2.700 |
| % Thioanisole conversion in 15 min. | 99.7 | 94.4 | 99.0 | 90.3 | 84.5 |

As apparent from Formulations 2-6, different compounds forming the decontamination composition were utilized.

Formula 7 sets forth a decontamination composition of the present invention wherein in lieu of a molybdate catalyst, a tungsten catalyst was utilized.

Formula 7

| Ingredient | g/100 mL |
|---|---|
| Sodium percarbonate | 4.650 |
| Potassium bicarbonate | 5.000 |
| Tergitol XH | 0.300 |
| Sodium lauroyl sarcosinate | 0.015 |
| Sodium tungsten oxide | 0.360 |
| Boric acid | 0.170 |
| Citric acid | 0.170 |
| Aspirin | 3.450 |

As apparent from Table 5, the reaction with respect to thioanisole proceeds slightly faster.

TABLE 5

Comparison of molybdate and tungsten against thioanisole.

|  | Reaction time | | |
|---|---|---|---|
|  | 5 min. | 15 mins. | 30 mins. |
| Molybdate | 72% conversion | 82% conversion | 99% conversion |
| Tungsten | 81% conversion | 98% conversion | 99% conversion |

Formula 8 does not contain an additional catalyst and was tested with regard to sporicidal efficacy against *Bacillus subtilis* spores on porcelain penicylinders as well as polyester and silk suture loops. Decon Green™ was utilized for comparison. The Tables below show comparative results.

Formula 8

|  | g/100 mL |
|---|---|
| Sodium Percarbonate | 3.850 |
| Potassium Bicarbonate | 1.925 |
| Tergitol 15-S-30 | 0.500 |

-continued

Formula 8

|  | g/100 mL |
|---|---|
| Boric Acid | 1.000 |
| Citric Acid | 1.000 |
| Aspirin | 2.700 |

Comparison of the sporicidal effectiveness of Formula 8 and Decon Green™ on polyester 7.48 baseline) and silk (6.75 baseline) suture loops using *Bacillus subtilis* spores is set forth in Table 6. The data represents the Average Log Reduction.

TABLE 6

|  | 1 hour |
|---|---|
| Formula 8 Polyester | 7.26 |
| Decon Green ™ Polyester | 6.90 |

TABLE 6-continued

|  | 1 hour |
|---|---|
| Formula 8 Silk | 6.75 |
| Decon Green™ Silk | 5.83 |

As apparent from the table, Formulation 8 of the present invention gave faster decontamination times.

As previously noted, it is preferred that the acetyl donor is coated with a coating material as described herein. Table 7 sets forth the results of coating aspirin at 40° C. with citric acid versus a Control wherein no citric acid was utilized. As apparent, a fairly significant amount of aspirin was lost after eight weeks of storage whereas only Y2 of 1% of aspirin was lost during the same time when coated with citric acid.

TABLE 7

Stability of aspirin at 40° C. that was coated with citric acid.

| % Aspirin (Initial) | % Citric Acid | % Aspirin Lost (8 weeks) |
|---|---|---|
| 100 | 0 | 8.4 |
| 86 | 14 | 0.5 |

As readily apparent, when a coating composition was not applied to the acetyl donor, a significant amount of the acetyl donor, i.e. aspirin, was lost in the initial eight week period after formulation of the decontamination composition.

The present invention thus relates to an effective one part, solids containing decontamination blend composition that can be readily shipped at low cost since it is light weight inasmuch as it contains no water. The composition is stable and safer than peracetic acid solutions and hydrogen peroxide solutions inasmuch as it does not contain any peracetic acid per se nor does it contain any peroxygen compound per se. Rather, it contains generally harmless precursors thereof. Another distinct advantage of the present invention is that it need not be formulated or activated until the actual site of application and then is readily made by simply adding water to the composition.

Another decided advantage of the present invention is that the dried decontamination composition of the present invention reacts very readily as by oxidizing the chemical or biological agent or warfare agent. For example, a 95%, or 97% or a 99% effective decontamination, eradication, etc., with regard to the chemical warfare agent such as soman (GD) or a biological agent such as *Bacillus subtilis* was achieved in 3 minutes or less, desirably in 2 minutes or less, and preferably even in 1 minute or less, by utilizing formulations of the present invention. In general, the compositions of the present invention also readily achieve at least about a 90% or 95% kill, eradication, etc., desirably at least about a 98% eradication, and preferably at least about a 99% decontamination or eradication of chemical and biological agents within 30 or desirably 15 minutes of application.

While in accordance with the patent statutes, the best mode and preferred embodiment have been set forth, the scope of the invention is not limited thereto, but rather by the scope of the attached claims.

What is claimed is:

1. A one part, solids blend decontamination composition for eradicating chemical or biological warfare agents, consisting of:

a. a solid acetyl donor consisting of acetylsalicylic acid, or encapsulated or non-encapsulated tetraacetylethylenediamine, or combinations thereof, which has been pre-coated, prior to mixing with the other solid components of the composition, with at least two alkaline hydrolysis resistant coating compounds, which are water soluble and are not themselves acetyl donors, consisting of: citric and boric acid;

wherein the coating is applied to the acetyl donor regardless of any pre-existing encapsulation, coating or other treatment utilized by a manufacturer of the acetyl donor; and b. a peroxygen source consisting of sodium percarbonate, sodium perborate, potassium percarbonate, or potassium perborate, or combinations thereof, wherein the amount of the acetyl donor utilized is from about 10% to about 70% by weight, based upon the total weight of the composition;

wherein the amount of the peroxygen source utilized is from about 10% to about 70% by weight, based upon the total weight of the composition;

wherein the total amount of the coating compounds utilized is from about 1% to about 20% by weight based, upon the total weight of the composition, and wherein the blend is complete in and of itself and is distributed as a single package product, which, when mixed with an existing water supply at the site of use, forms a peracetic acid-containing solution having a concentration of peracetic acid of at least about 0.5% to about 15% by weight and a peroxygen concentration of from about 0.5% to about 15% by weight, based upon the total weight of the blend and water.

2. The decontamination composition according to claim 1, wherein the peroxygen source is sodium percarbonate.

3. The decontamination composition according to claim 2, wherein the amount of the acetyl donor is from about 20% to about 35% by weight, wherein the total amount of the coating compounds is from about 1.5% to about 10% by weight, wherein the amount of the peroxygen source is from about 20% or 30% to about 45% or 50% by weight, based upon the total weight of the composition, and wherein the blend when mixed with water forms a solution having a concentration of peracetic acid of from about 1% to about 3% by weight and a peroxygen concentration of from about 1% to about 3% by weight, based upon the total weight of the blend and water.

4. The decontamination composition according to claim 1, wherein the composition is a free-flowing powder composition or an integral solid.

5. The decontamination composition according to claim 3, wherein the composition is a free-flowing powder composition or an integral solid.

6. The decontamination composition according to claim 1, wherein the composition, when reacted with water, oxidizes chemical or biological agents comprising mustard gas HD (bis (2-chloroethyl) sulfide; nerve gas VX (S-[2-[bis-(1-methylethyl)amino]ethyl] o-ethyl-methyl phos-phonothioic acid ester), soman (1,2,2-trimethylpropyl methylphosphonofluoridic acid ester), a blistering agent, thioanisole, small pox virus, polio virus, pneumonia-causing biological agents or toxins, anthrax, ricin, T-2-mycotoxin, toxic industrial materials, toxic industrial chemicals, bird flu, *C. difficile*, HIV, endospores comprising *Geobacillus stearothermophilus*, *Bacillus subtilis*, *Bacillus subtilis globigii*, *Clostridium sporogenes*, *Bacillus cereus*, and *Bacillus circulans*, fungi comprising *Aspergillus niger*, *Candida albicans*, *Trichophyton mentagrophytes*, and *Wangiella dermatitis*, mycobacteria comprising *Mycobacterium* chelonae, *Mycobacterium gordonae, Mycobacterium smegmatis*, and *Mycobacterium terrae*, vegetative bacteria comprising *Aeromonas hydrophila, Enterococcus faecalis, Streptococcus faecalis, Enterococcus faecium, Streptococcus pyogenes, Escherichia coli, Klebsiella pneumoniae, Legionella pneumophila, Methylobacterium, Pseudomonas aeruginosa, Salmonella choleraesuis, Helicobacter pylori, Staphylococcus aureus, Staphylococcus epidermidis*, and *Stenotrophomonas maltophilia*, protozoa comprising *Giardia lamblia* and *Cryptosporidium parvum*, prions comprising infectious proteins, or combinations thereof.

7. The decontamination composition according to claim 3, wherein the composition, when reacted with water, oxidizes a chemical or biological agent, and wherein the chemical or biological agent comprises mustard gas HD (bis(2-chloroethyl) sulfide; nerve gas VX (S-[2-[bis-(1-methyl-ethyl)amino]ethyl] o-ethyl-methyl phosphonothioic acid ester), soman (1,2,2-trimethyl-propyl methylphosphonofluoridic acid ester), a blistering agent, thioanisole, a virus, pneumonia-causing biological agents or toxins, anthrax, ricin, T-2-mycotoxin, toxic industrial materials, toxic industrial chemicals, bird flu, *C. difficile*, HIV, endospores comprising *Geobacillus stearothermophilus, Bacillus subtilis, Bacillus subtilis* globigii, *Clostridium sporogenes, Bacillus cereus*, and *Bacillus circulans*, fungi comprising *Aspergillus niger, Candida albicans, Trichophyton mentagrophytes*, and *Wangiella dermatitis*, mycobacteria comprising *Mycobacterium* chelonae, *Mycobacterium gordonae, Mycobacterium smegmatis*, and *Mycobacterium terrae*, vegetative bacteria comprising *Aeromonas hydrophila, Enterococcus faecalis, Streptococcus faecalis, Enterococcus faecium, Streptococcus pyogenes, Escherichia coli, Klebsiella pneumoniae, Legionella pneumophila, Methylobacterium, Pseudomonas aeruginosa, Salmonella choleraesuis, Helicobacter pylori, Staphylococcus aureus, Staphylococcus epidermidis*, and *Stenotrophomonas maltophilia*, protozoa comprising *Giardia lamblia* and *Cryptosporidium parvum*, prions comprising infectious proteins, or combinations thereof.

8. A one-part, solid powder blended decontamination composition for eradicating chemical or biological warfare agents, consisting of:
   a. sodium percarbonate, present in an amount of from about 10 to about 70% by weight, based on the total weight of the composition;
   b. an acetyl donor consisting of acetylsalicylic acid or encapsulated or non-encapsulated tetraacetylethylenediamine, or mixtures thereof, which has been pre-coated, prior to mixing with other solid components of the composition, with at least two coating compounds consisting of citric acid and boric acid, wherein the amount of the acetyl donor utilized is from about 10% to about 70% by weight, based upon the total weight of the composition, and wherein the coating compounds are present in equal amounts and the total amount of coating compounds utilized is from about 1 to about 20% by weight, based upon the total weight of the composition;
   c. a buffer consisting of potassium bicarbonate, borax, a monobasic phosphate, or mixtures thereof; and
   d. a surfactant consisting of sodium lauroyl sarcosinate, a polyether polyol, an ethylene oxide/propylene oxide copolymer, or mixtures thereof,
   wherein the blend is complete in and of itself and is distributed as a single package product, which when mixed with an existing water supply on site forms a peracetic acid-containing solution having a concentration of peracetic acid of at least about 0.5%, based upon the total weight of the blend and water.

9. A one-part, solid powder blended decontamination composition for eradicating chemical or biological warfare agents, consisting of:
   a. a solid peroxygen source, consisting of sodium percarbonate, sodium perborate, potassium percarbonate, or potassium perborate, or combinations thereof, present in an amount of from about 20 or 30% to about 45 or 50% by weight, based upon the total weight of the composition;
   b. at least one acetyl donor, consisting of acetylsalicylic acid, encapsulated or non-encapsulated tetraacetylethylenediamine, or mixtures thereof, wherein the acetyl donor has been pre-coated, prior to mixing with other solid components of the composition, with at least two coating compounds consisting of citric acid and boric acid, wherein the amount of the acetyl donor utilized is from about 20% to about 35% by weight and the total amount of coating compounds utilized is from about 1.5% to about 10% by weight, based upon the total weight of the composition;
   c. a buffer consisting of potassium bicarbonate, borax, a monobasic phosphate, or combinations thereof, present in an amount from about 5 to about 50% by weight, based upon the total weight of the composition;
   d. a surfactant consisting of an anionic surfactant, a nonionic surfactant, or an amphoteric surfactant, or mixtures thereof, present in an amount from about 0.01% to about 10% by weight, based upon the total weight of the composition; and
   e. a catalyst consisting of a molybdate compound or a tungsten compound, wherein the blend is complete in and of itself and is distributed as a single package product, which when mixed with an existing water supply on site forms a solution having a concentration of peracetic acid of at least about 0.5%, based upon the total weight of the blend and water.

10. The decontamination composition of claim 9, wherein the surfactant consists of sodium lauroyl sarcosinate, a polyether polyol, an ethylene oxide/propylene oxide block copolymer, or mixtures thereof.

* * * * *